United States Patent [19]

Dolnick et al.

[11] Patent Number: 4,896,143
[45] Date of Patent: Jan. 23, 1990

[54] GAS CONCENTRATION SENSOR WITH DOSE MONITORING

[75] Inventors: Earl M. Dolnick, Encinitas; Terry G. Anderson, San Diego, both of Calif.

[73] Assignee: Quantum Group, Inc., San Diego, Calif.

[21] Appl. No.: 42,264

[22] Filed: Apr. 24, 1987

[51] Int. Cl.[4] .............................................. G08B 17/10
[52] U.S. Cl. .................................... 340/634; 73/27 R; 364/571.07
[58] Field of Search .................... 340/634, 633; 73/23, 73/27 R, 25-27 R, 27 A; 374/142; 324/425; 364/581, 571.07, 571.01, 571.03, 571.04

[56] References Cited

U.S. PATENT DOCUMENTS

| | | | |
|---|---|---|---|
| 3,676,820 | 7/1972 | Taguchi | 338/34 |
| 3,906,473 | 9/1975 | Le Vine | 340/634 |
| 4,123,700 | 10/1978 | LaConti et al. | 324/425 |
| 4,185,491 | 1/1980 | Owen | 340/634 |
| 4,419,021 | 12/1983 | Terada et al. | 324/142 |
| 4,446,718 | 5/1984 | Bukowiecki et al. | 73/23 |
| 4,457,161 | 7/1984 | Iwanaga et al. | 73/23 |
| 4,567,475 | 1/1986 | Bukowiecki et al. | 340/634 |
| 4,592,967 | 6/1986 | Komatsu et al. | 340/634 |
| 4,703,646 | 11/1987 | Müller et al. | 73/23 |

OTHER PUBLICATIONS

Figaro Gas Sensor TGS, Figaro Engineering, Inc.—7 pages, Sep. 20, 1976.
Figaro Gas Sensor TGS 203, Figaro Engineering, Inc.—17 pages.

Primary Examiner—Joseph A. Orsino
Assistant Examiner—Jill D. Jackson
Attorney, Agent, or Firm—Christie, Parker & Hale

[57] ABSTRACT

A tin oxide carbon monoxide sensor is operated in a manner to exclude effects of ambient temperature and humidity. Resistance of the sensor is measured at a lower temperature and again at a higher temperature. The target gas concentration is determined as a function of the first and second resistances, thereby cancelling the effects of humidity and ambient temperature.

10 Claims, 1 Drawing Sheet

GAS CONCENTRATION SENSOR WITH DOSE MONITORING

BACKGROUND OF THE INVENTION

The use of metallic oxide semiconductor sensors for the detection of various gases and vapors is well known. For many years, a Japanese company, Figaro Engineering Co., Inc. of Osaka, Japan, has been manufacturing and marketing a family of such sensors based upon Tin Oxide for gas detection as described in U.S. Pat. No. 3,676,820. In practice the resistance of the tin oxide is measured, usually while it is heated. The resistance changes dramatically when even small amounts of organic vapors, Carbon Monoxide, or even water vapor are present.

The utility of these sensors for use as Carbon Monoxide detectors is frequently compromsied by their sensitivity to these other gases, by changes of the sensor resistance due to ambient temperature and humidity and by the tendency of the sensor to saturate with exposure even to low concentrations of gas if such levels persist for a long enough time.

Recently a method has been disclosed by Le Vine, U.S. Pat. No. 3,906,473 which enhances the sensitivity to CO of these sensors, while reducing responses from undesired organic vapors and reducing the possibility of saturation. The method consists of operating the sensor in a cyclic manner wherein the tin oxide sensor is heated to a high temperature for a short period of time, followed by another period at a lower temperature. The resistance of the tin oxide sample is measured at the end of the lower temperature period. The theory as disclosed in the patent is that the high temperature purges the sensor, driving off the volatile components and returning the sensor to its high impedance state. Then, when the sensor cools to the lower temperature, where it is more sensitive to CO, a more accurate measurement of CO can be made. Since the sensor is continuously cycled between the two temperatures, saturation of the sensor is prevented. While the Le Vine method is an improvement in Tin Oxide sensor operation, compensation still must be made for changes in ambient temperature, usually by means of a thermistor matched to the temperature coefficient of tin oxide. Additionally the tin oxide is subject to changes in response if the humidity changes, requiring humidity compensation which is neither simple nor inexpensive.

Such sensitivity problems have limited the application of these sensors. The possibility of false alarms prevents the use of such sensors in critical applications such as automatic shutoff devices for combustion appliances.

The present invention is a novel improvement in the method of Le Vine as discussed above. This improvement compensates for response changes due to changes in ambient temperature and humidity, allowing operation from below 15% to above 90% relative humidity and from below 0 degrees C. to above 50 degrees C. without the need for additional compensating elements. This improvement also increases the accuracy of the CO measurement, allowing these inexpensive sensors to be used for quantitative measurement of CO concentration. Inexpensive devices can now be built which measure the time weighted average of CO concentration. Such devices much more accurately model the physiological effects of CO and thus can more easily determine when the CO dose has reached a dangerous level. Present devices to perform this function are based on expensive and short lived electrochemical sensors, but since they can now be made with inexpensive tin oxide sensors using this novel method, very low priced CO alarms can be easily produced. Safety shutoff systems for combustion devices can now be built using this novel method to provide a very high degree of freedom from false alarms.

SUMMARY OF THE INVENTION

This novel method utilizes a similar high/low temperature cyclic mode as described in the Le Vine patent. However, the current supplied to the sample heaters for the purpose of heating the sample is not constant but rather is supplied as a series of pulses. The pulses heat the sensor to the same temperature as if the current were constant, but now, there are periods between the pulses when the current is not flowing. Those periods may be used for the measurement of the the sensor resistance.

For the measurement of CO it has been found that only two measurements of the resistance, one at high temperature and one at low temperature, need be made instead of a more complex measuring scheme. As above, the measurements are made during the time intervals between current pulses when the current is not flowing. The resistance measurements made just after the high current interval are more dependent on ambient temperature and humidity than CO concentration. The measurement made at the end of the low current interval is relatively more sensitive to CO than humidity. The ambient temperature affects both measurements. By making these two measurements, the effect due to humidity can be deduced by suitable computation, and compensation can be mathematically performed. Since the same sensor is used for both measurements, the effect of ambient temperature is cancelled, and no external compensation elements are necessary.

As stated above, gas sensors based upon Tin Oxide are also sensitive to gases other than CO. Since the sensitivity to each of these gases has a different temperature dependence, measuring the sensor resistance at various temperatures may be used to facilitate the measurement of the concentration of these gases.

THE DRAWINGS

A block diagram of one type of sensor configuration for the practice of this method is shown in FIG. 1. A portion of the block diagram of FIG. 1 is shown in FIG. 2.

DESCRIPTION OF THE DRAWINGS

One example of a sensor that may be utilized with this method is the gas sensor TGS 109 manufactured by the Figaro Engineering Co. as mentioned above. It has within it a Tin Oxide block suspended between two wires which serve as both heaters and as electrodes for the the sensor resistance measurement.

Figure 1:
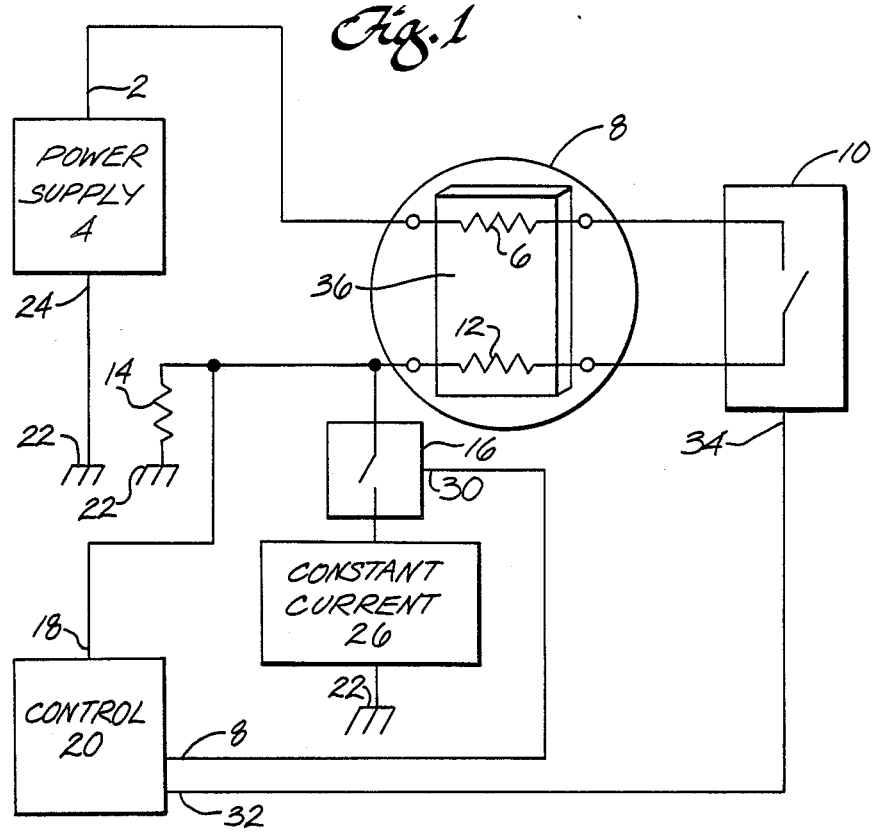
In FIG. 1 a positive conductor 2 of a power supply 4 is connected to one side of a first heater element 6 of a conventional Tin Oxide gas sensor 8. The other side of the heater 6 is connected one side of a sensor electronic switch 10. The other side of the electronic switch 10 is connected to one side of a second heater element 12 of the sensor 8. The other side of the heater 12 is connected to one end of a load resistor 14, to one side of a regulator electronic switch 16 and to an analog input 18 of a measurement and control circuit 20.

The sensor heaters 6 and 12 are mounted within the Tin Oxide block 36 which is contained within the sensor 8. The other side of the resistor 14 is connected to a ground 22. Also connected to the ground 22 is the negative output conductor 24 of the power supply 4, and the output of a current regulator circuit 24, which can assure constant current flow. One control output 28 of the measurement and control circuit 20 is connected to the control input 30 of the regulator electronic switch 16 and the other control output 32 of the measurement and control circuit 20 is connected to the control input 32 of the sensor electronic switch 10.

The measurement system works in the following manner. The measurement and control circuit 20 sends a signal from the output 28 to the control input 30 of the sensor electronic switch 16 causing it to close. At the same time, a signal from the control output 32 to the control input 34 of the sensor electronic switch 10 causes it to close. Current now flows from the power supply 4 via the conductor 2, through the heater 6, the switch 10, the switch 16 and the constant current circuit 26, returning through the ground connection 22. While current is flowing, the constant current circuit 26 acts to regulate the current so that it remains constant. The current flowing through the heaters 6 and 12 heats the Tin Oxide block 36. By controlling the operation of the electronic switches 10 and 16, the measurement and control circuit can vary the duty cycle of the current. Thus, by periodically and regularly turning the current on and off, the average current can be set to any desired value.

Figure 2:
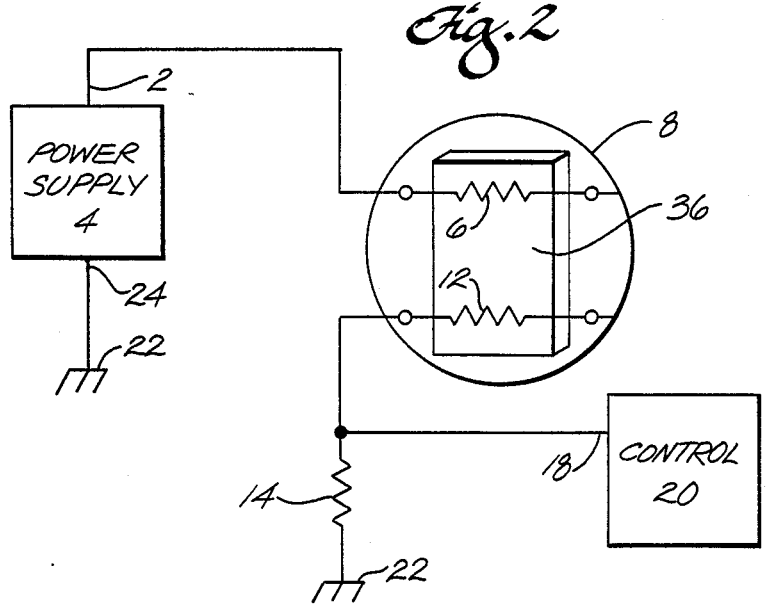

Further, when the switches 10 and 16 are both open the circuit reduces to that of FIG. 2. The current now passes through the Tin oxide block 36 and through the resistor 14. The analog input 18 of the measurement and control circuit 20 now measures the voltage drop across the resistor 14 caused by the current flowing through the Tin Oxide block 36. The voltage drop is functionally dependent on the Tin Oxide resistance. Thus, it will be recognized that the resistance of the Tin Oxide block need not be measured directly but a property of the system that is a function of the resistance may be measured instead.

In practice of the method, the current is first set to be high by closing switches 10 and 16. The resulting current is regulated by the regulator circuit 26 to a value of 370 milliamperes. After one minute the current is reduced to a value 25% as great by periodically turning the switches 10 and 16 on and off such that the 370 milliampere current flows for only 25% of the time, producing a current with an average value of 92.5 milliamperes. This lower average current is allowed to flow for 1.5 additional minutes. The high current and low current periods are sufficiently long that the Tin Oxide block 36 is in thermal equilibrium first at a high temperature when the current is high and then also at a lower temperature after the current is reduced. The voltage drop measurement is made at the end of the high current period and at the end of the low current period.

At the time of sensor measurement, the effective circuit is a portion of FIG. 1 and that portion is shown in FIG. 2. As described above the heaters 6 and 12 now become electrodes for the sensor resistance measurement. The computation method is based upon the voltage measured at the the junction of the second heater electrode 12 and the resistor 14. If V is the voltage measured, then it relates to the sensor resistance by:

$$V = (R/(R+S))Vps \quad (1)$$

where R is the value of the resistor 14, S is the resistance of the tin oxide sample 24 and Vps is the voltage of the power supply 4. In the preferred embodiment of the method the measurement and control circuit is a digital microprocessor. The voltage V is measured by an analog to digital converter within the microprocessor and hence is quantized into 256 discrete integer values.

Let X be the integer value of V measured when the sensor is at the high temperature, and let Y be the integer value of V when the sensor is at the low temperature. Further, since high resolution is not necessary, let X be further quantized into 16 discrete levels and offset to numbers between 5 and 20. In the same manner, since the Y measurement shows a greater dynamic range, Y is quantized into 32 discrete levels and offset to numbers between $-34$ and $-3$. With X and Y measured and configured in this way, the integer value of CO concentration in parts per million, independent of humidity, was empirically determined to be:

$$CO(ppm) = -22 - 252/Y + 835/X - 32700/(XY) \quad (2)$$

where the value of CO in parts per million is an integer with numbers between 0 and 255. The empirical determination was made by studying the performance of the Tin Oxide gas sensors under variations of temperature, humidity and CO concentration. Tests were conducted from 0 deg. C. to 50 deg. C., from 5% to 95% relative humidity and 0 to 250 parts per million of CO.

For ease of use with microprocessor based CO measuring instruments, equation (2) may be solved for various values of X and Y and the results formed into a rectangular array of values (X,Y) which is then loaded into the microprocessor memory. Then, when the method is practiced and the values of X and Y are measured, they point to a unique value in the array which is the concentration of CO independent of ambient temperature and humidity. Alternately the equation (2) may be solved in real time for the value of CO once the values of X and Y are determined.

In order to form the time weighted average or other dose calculation method, the values of CO that are measured may be accumulated over time. Since the sensor heating cycle forms a fixed time interval, a dose measurement may be made by adding the measured value of CO concentration to a memory register each time the value is determined. An alarm is issued if the accumulated value reaches a predetermined value.

The desired accumulation function may be implemented by modifying the values added based upon a weighting function dependent upon the measured concentration. For example, low levels of CO that are not physiologically significant such as those below 50 parts per million may not be added and may even be subtracted from the accumulation register. On the other hand, high values such as 200 ppm. may be increased such as by doubling or more before addition to the register takes place. Thus, the dose measurement may be adjusted to closely match the physiological response of the human body to CO, producing a more effective device and enhancing the resistance to false alarms.

This method may be effectively applied to devices other than alarms. For example actions may be initiated such as shutting off the flow of fuel gas to a combustion appliance, or opening a vent or the like.

If desired, the present method may be calibrated for CO levels greater than 255 parts per million. However, for most purposes, it is not necessary to differentiate different levels of CO when the concentration is high since any levels greater than 250 parts per million are sufficiently dangerous that an immediate alarm would be warranted.

Other sensors are available wherein the sensitivity is modified with respect to various target gases including CO by the addition of certain dopant materials to the Tin Oxide formulation. These sensors may be easily used with this method and obtain all the benefits herein described although equation (2) might need to be empirically adjusted so that the proper values are determined.

The method herein described measures two voltages which are related to the sensor resistance. The method may be applied equally well to measurements of other parameters such as the sensor current or other parameter related to the sensor resistance.

Although the method has been described in terms of measuring two resistances at two different temperatures, it will be apparent that enhanced results may be provided by making three or more measurements at different temperatures and correlating the results. Many measurements may be made, and may be extended to a continuous measurement of the rate of change of sensor resistance with respect to temperature, the method applying equally well in all cases.

This method brings improved accuracy to low cost measurements of Carbon Monoxide. The improved accuracy allows a dose measurement to be made, which greatly reduces the possibility of false alarms while still providing protection against a significant danger of CO poisoning.

We claim:

1. A method for measuring a target gas concentration comprising:
    measuring the resistance of a conductive metal oxide gas sensor exposed to a target gas at a first, relatively lower equilibrium temperature;
    measuring the resistance of the conductive metal oxide gas sensor exposed to the target gas at a second, relatively higher equilibrium temperature; and
    solving an equation for determining a plurality of values of target gas concentration as a function of resistance values, storing in a memory a plurality of such target gas concentration values as a function of resistance values, and using both of the measured resistance values to look up in the memory a value of target gas concentration.

2. A method for measuring a target gas concentration comprising:
    measuring the resistance of a conductive metal oxide gas sensor exposed to a target gas at a first, relatively lower equilibrium temperature;
    measuring the resistance of the conductive metal oxide gas sensor exposed to the target gas at a second, relatively higher equilibrium temperature; and
    solving an equation for target gas concentration as a function of both measured resistances for determining target gas concentration as a function of at least the first and second resistances.

3. A method as recited in claim 2 comprising measuring the resistance of the gas sensor exposed to the target gas at a third temperature different from the first and second temperatures and determining target gas concentration as a function of said first, second and third temperatures.

4. A gas concentration sensor system comprising:
    a conductive metal oxide gas sensor having resistance which is variable in response to gas concentration, including concentration of a target gas;
    means connected to the gas sensor for measuring a first resistance of the gas sensor at a lower temperature;
    means connected to the gas sensor for intermittently heating the gas sensor from the lower temperature to a higher temperature;
    means connected to the gas sensor for measuring a second resistance of the gas sensor at the higher temperature;
    means connected to the measuring means for determining target gas concentration as a function of both the first and second resistances;
    register means for accumulating values of target gas concentration from the determining means;
    means for adding values to the register means when target gas concentration exceeds a selected value; and
    means for subtracting values from the register means when target gas concentration is less than the selected value.

5. A gas concentration sensor system as recited in claim 4 wherein the gas sensor comprises an electrically heated tin oxide sensor having resistance variable in response to carbon monoxide concentration.

6. A gas concentration sensor system as recited in claim 4 wherein the means for determining target gas concentration comprises means for storing an array of values of target gas concentration as a function of both the first and second resistances, and means for looking up the value of target gas concentration unique to specific first and second resistance values.

7. A gas concentration sensor system as recited in claim 4 wherein the means for determining target gas concentration comprises means for solving an equation for target gas concentration as a function of both the first and second resistances.

8. A method for monitoring carbon monoxide concentration comprising:
    periodically measuring concentration of carbon monoxide;
    adding to a digital register when the concentration exceeds a selected value; and
    subtracting from the digital register when the concentration is less than the selected value.

9. A method as recited in claim 8 comprising weighting at least some carbon monoxide concentrations before adding to or subtracting from the register.

10. A method as recited in claim 8 wherein the addition to and subtraction from in the register are matched to the physiological response of the human body to carbon monoxide.

* * * * *